US011131681B2

(12) United States Patent
Park et al.

(10) Patent No.: US 11,131,681 B2
(45) Date of Patent: Sep. 28, 2021

(54) METHOD FOR DIAGNOSING PSYCHIATRIC DISORDERS

(71) Applicant: SPHINGO BRAIN CO., LTD., Daejeon (KR)

(72) Inventors: Byeong Deog Park, Daejeon (KR); Se Kyoo Jeong, Daejeon (KR); Kyungho Park, Seoul (KR); Chae Hyeong Park, Daejeon (KR); Kyong Oh Shin, Cheongju (KR)

(73) Assignee: DR. RAYMOND LABORATORIES, INC., Englewood Cliffs, NJ (US)

( * ) Notice: Subject to any disclaimer, the term of this patent is extended or adjusted under 35 U.S.C. 154(b) by 279 days.

(21) Appl. No.: 15/981,669

(22) Filed: May 16, 2018

(65) Prior Publication Data

US 2018/0259542 A1    Sep. 13, 2018

Related U.S. Application Data

(63) Continuation of application No. PCT/KR2018/002836, filed on Mar. 9, 2018.

(30) Foreign Application Priority Data

Mar. 10, 2017 (KR) .................. 10-2017-0030692

(51) Int. Cl.
*G01N 33/92* (2006.01)
*G01N 33/50* (2006.01)

(52) U.S. Cl.
CPC ......... *G01N 33/92* (2013.01); *G01N 33/5088* (2013.01); *G01N 33/5091* (2013.01); *G01N 2405/08* (2013.01); *G01N 2800/30* (2013.01); *G01N 2800/305* (2013.01); *G01N 2800/50* (2013.01)

(58) Field of Classification Search
CPC .......... G01N 2405/30; G01N 2800/30; G01N 2800/304; G01N 2800/305; G01N 2800/50; G01N 33/5088; G01N 33/5091; G01N 33/92; G01N 33/48; G01N 33/4833

USPC .................... 436/63, 71, 161, 173
See application file for complete search history.

(56) References Cited

U.S. PATENT DOCUMENTS

| | | | |
|---|---|---|---|
| 7,906,300 B2* | 3/2011 | Thiruvengadam | C12Q 1/34 435/18 |
| 2012/0149038 A1* | 6/2012 | Grubb | G01N 33/6896 435/7.92 |
| 2016/0209428 A1* | 7/2016 | Naviaux | A61K 31/185 |
| 2018/0059127 A1* | 3/2018 | Indra | A61K 9/0014 |
| 2018/0224470 A1* | 8/2018 | Leung | G01N 33/92 |

OTHER PUBLICATIONS

Smesny et al. Schizophrenia Bulletin, vol. 39, No. 4, May 15, 2012, pp. 933-941.*
Henriquez-Henriquez et al. Frontiers in Neuroscience, vol. 9, article 300, Aug. 25, 2015, pp. 1-9.*
Borodzicz et al. Lipids in Health and Disease, vol. 15:13, 2016, pp. 1-9.*
Wang et al. Journal of Psychiatry Neuroscience, vol. 41 (1), Sep. 22, 2015, pp. 27-37.*
Clausen et al. Scientific Reports, vol. 6:19918, Jan. 28, 2016, pp. 1-8.*
Van der Molen et al. Arch. Dermatol. Research, vol. 289, 1997, pp. 514-418.*
Escobar-Chavez et al. Journal of Pharm. Pharmaceut. Science, vol. 11(1), Mar. 24, 2008, pp. 104-130.*
Olesen et al. Scientific Reports, vol. 9:12217, Aug. 21, 2019, pp. 1-6.*
Lademann et al. European Journal of Pharmaceutics and Biopharmaceutics, vol. 72, Aug. 19, 2008, pp. 317-323.*

* cited by examiner

*Primary Examiner* — Maureen Wallenhorst
(74) *Attorney, Agent, or Firm* — Simi Law Group, P.C.

(57) ABSTRACT

Disclosed herein is a method for predicting or diagnosing psychiatric disorders through analyzing skin tissues samples minimally invasive or non-invasively collected. The method disclosed herein makes it possible to diagnose psychiatric disorders through objective biomarkers at a very early age, without giving pain to subjects because of noninvasive or minimally invasive feature of skin sample collection method.

3 Claims, 7 Drawing Sheets

[FIG. 1]
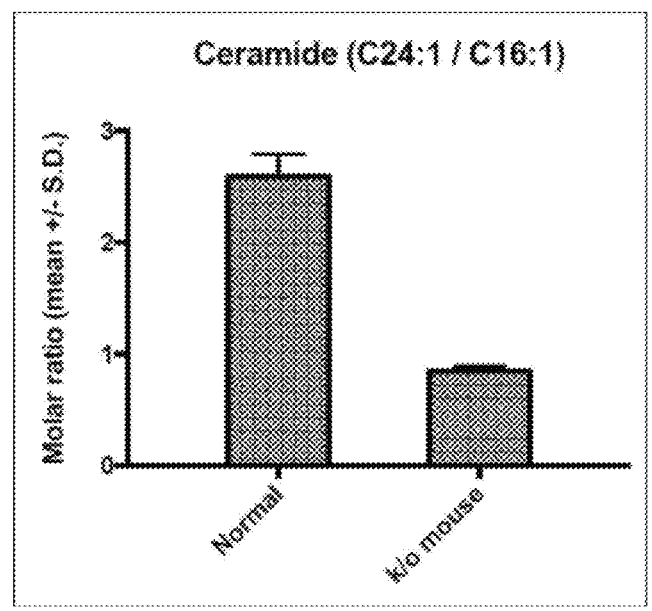
[FIG. 2]
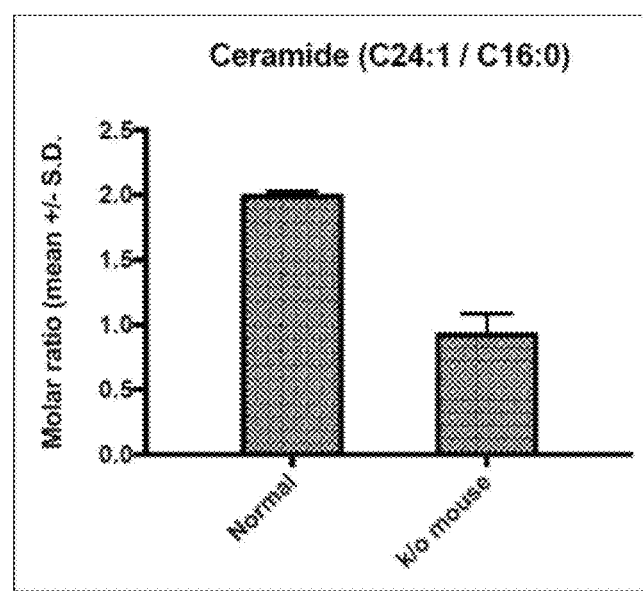

[FIG. 3]
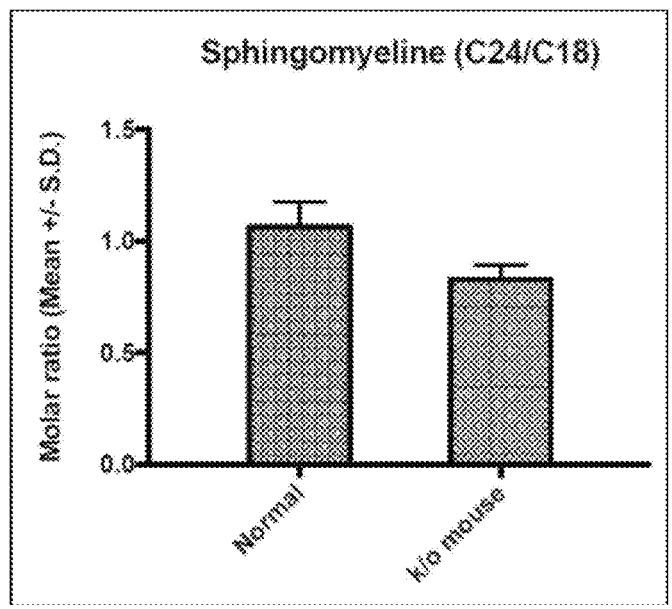
[FIG. 4]
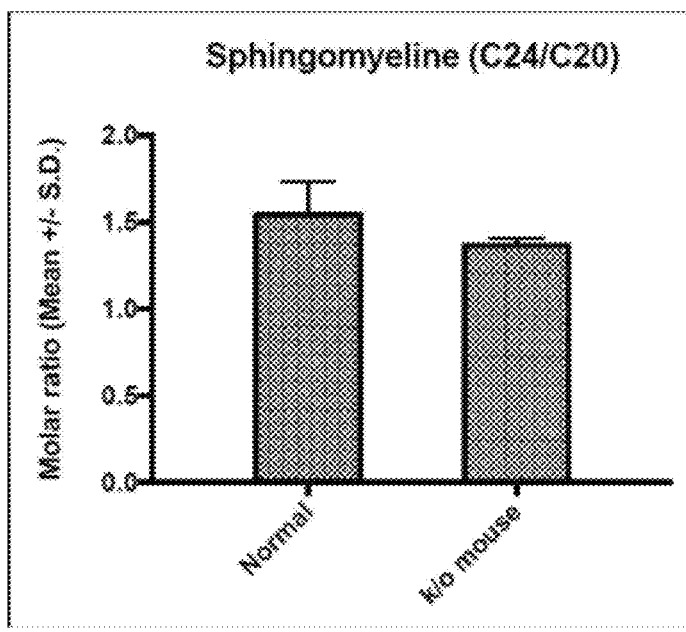

[FIG. 5]
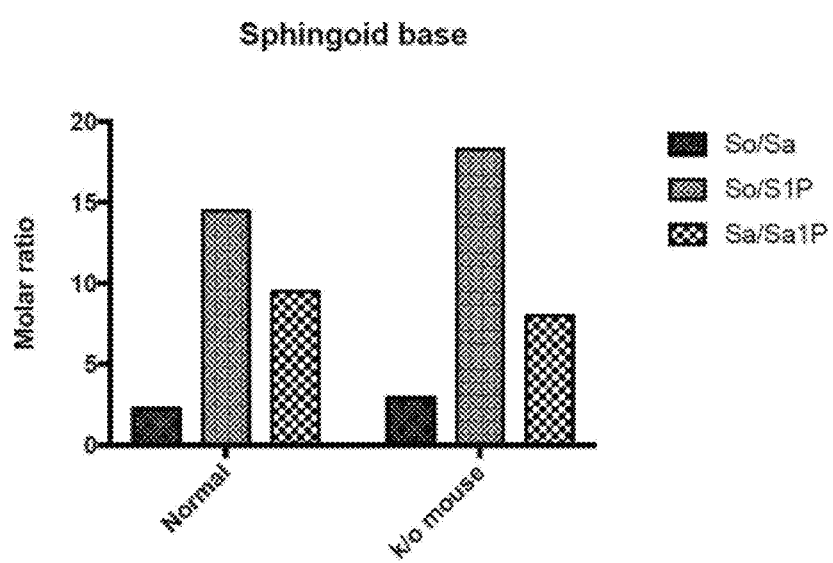

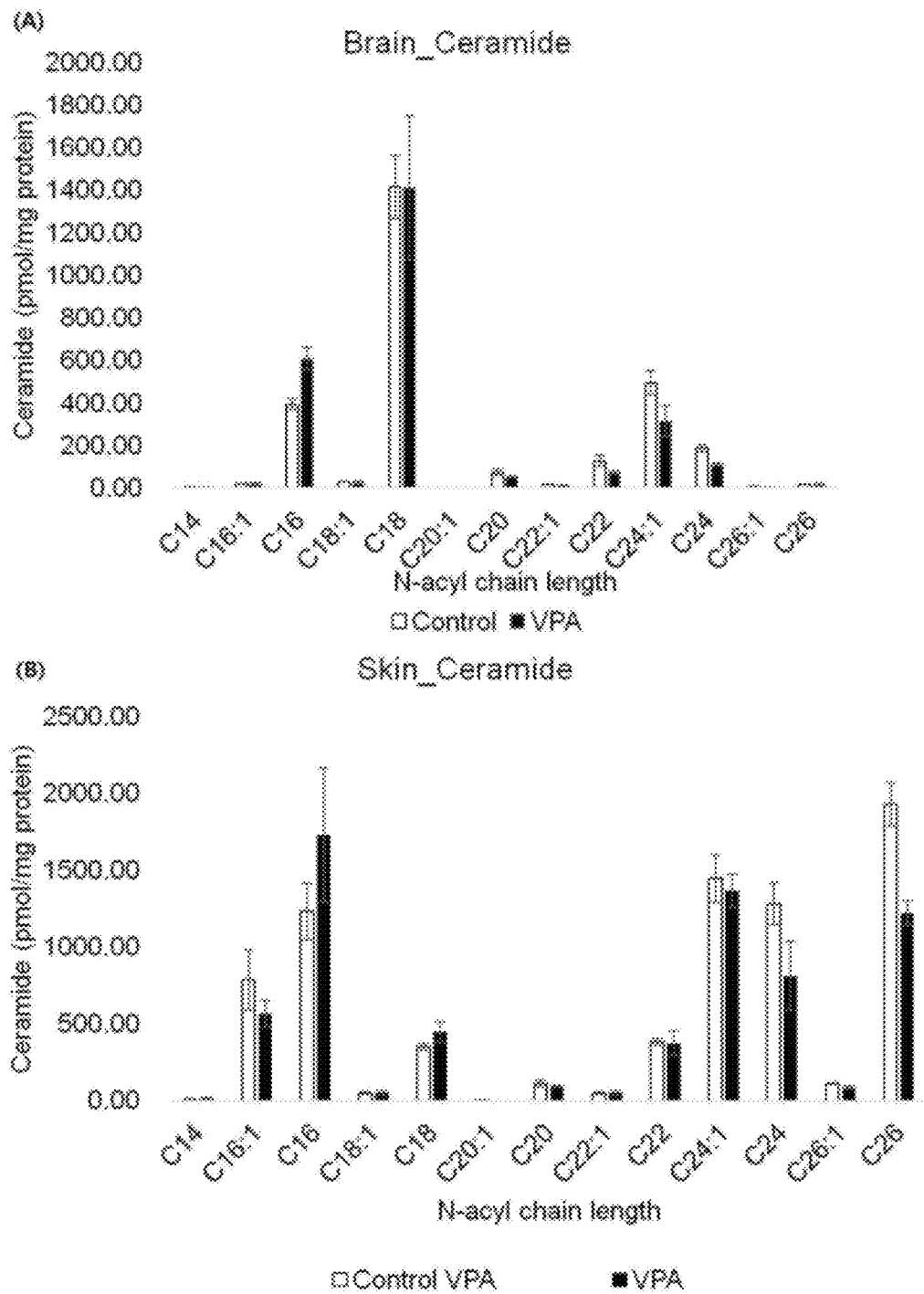
[FIG. 6]

[FIG. 7]
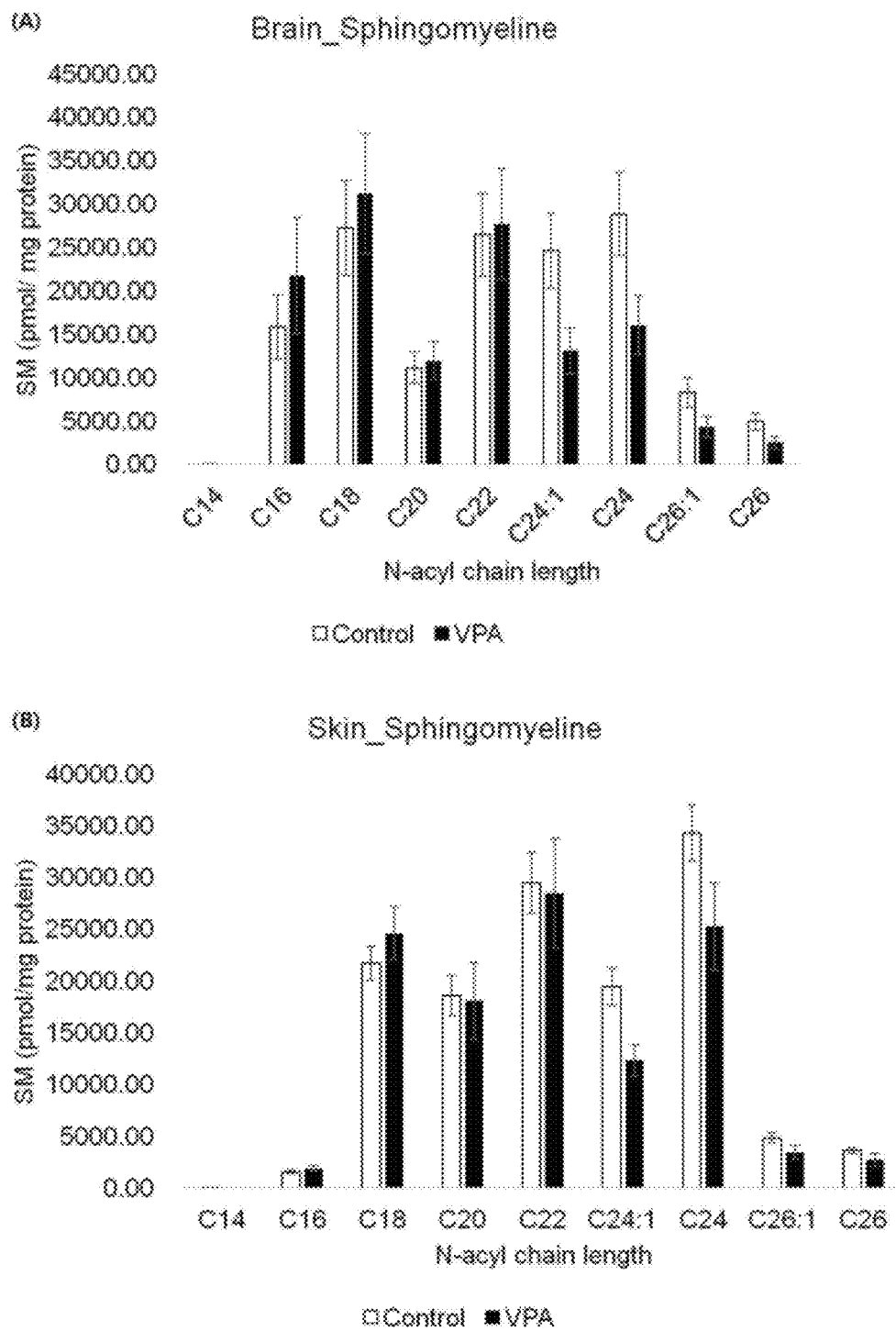

[FIG. 8]
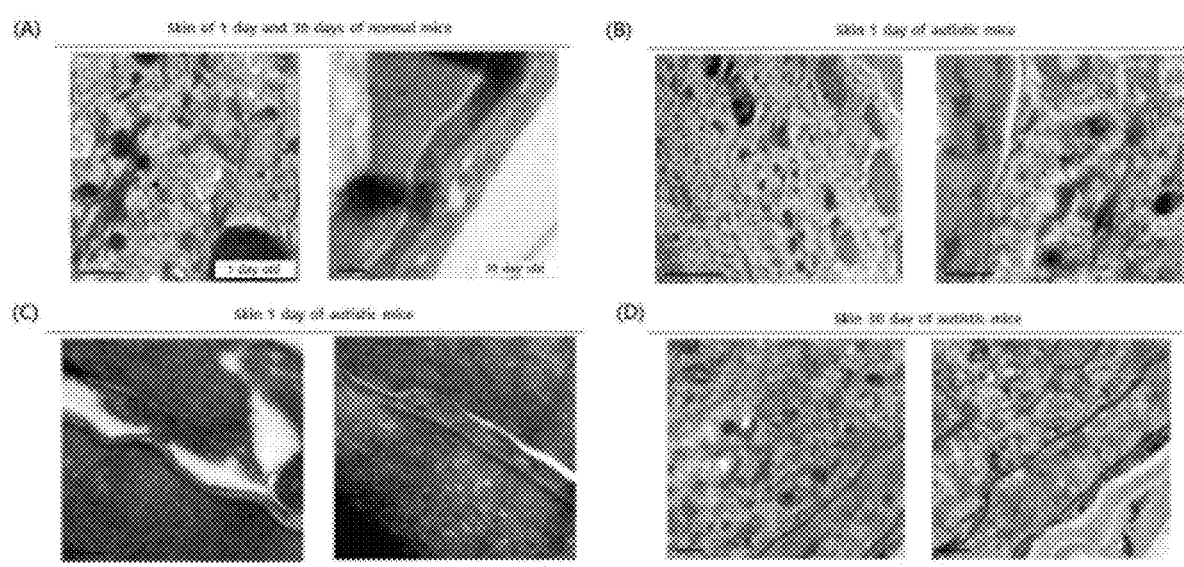

[FIG. 9]
(A)
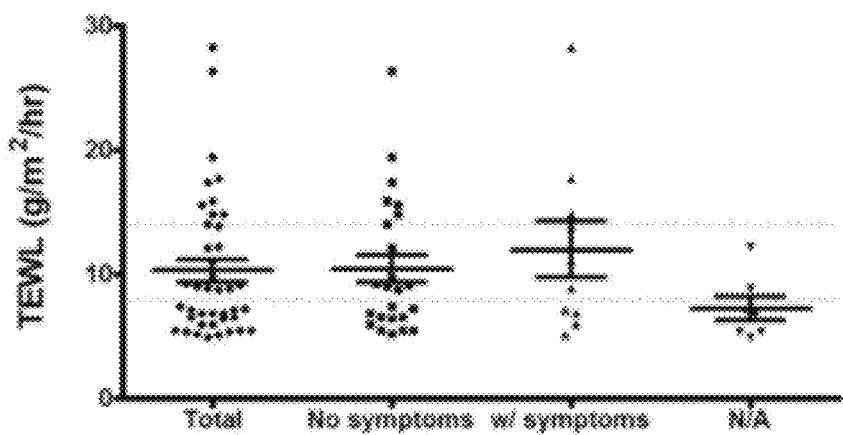
(B)
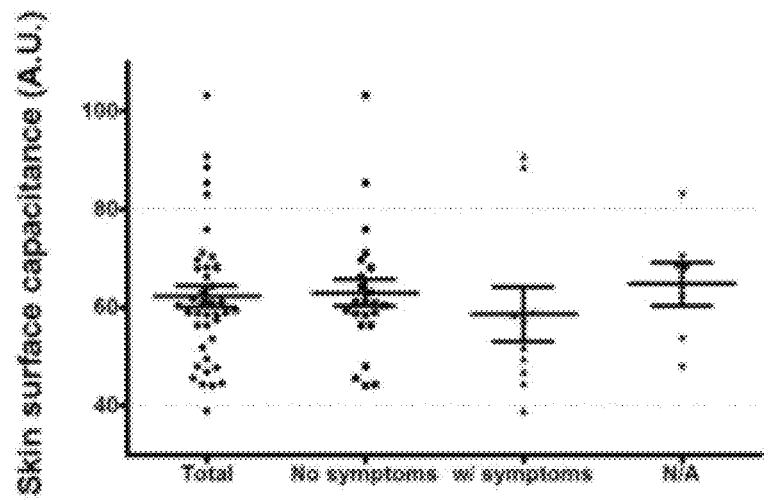

METHOD FOR DIAGNOSING PSYCHIATRIC DISORDERS

BACKGROUND OF THE INVENTION

This application is a continuation of PCT/KR2018/002836, filed on Mar. 9, 2018, which claims priority to Korean Patent Application No. 10-2017-0030692, filed on Mar. 10, 2017, which is incorporated by reference for all purposes as if fully set forth herein.

TECHNICAL FIELD

Description of the Related Art

Psychiatric disorders can be caused by an external trauma. Inappropriate stimulation from the surrounding environment from infancy to childhood, either excessive or insufficient, is also considered as a causable factor for psychiatric disorder. Genetic factor is another important one for triggering or exacerbating psychiatric disorders. For example, the causes of developmental disorders such as autism have not been clearly identified but it is known that they can be caused by complex interactions between genetic factors and environmental factors.

For many psychiatric disorders including autism spectrum disorder, it takes a significant time to clearly identify the specific behavioral patterns of the psychiatric disorders and, particularly, there are only a few techniques developed to diagnose the psychiatric disorders in the early infancy. In the case of developmental disorders such as autism, the onset of the disorders is predicted or diagnosed by observing and analyzing the behaviors of the suspected person. However, biomarkers that can predict or diagnose the onset of the disorders are not well known and often not accurate enough.

In the case of the psychiatric disorders, which are highly affected by environmental factors, the early diagnosis of the disorder can improve the treatment results. For example, integrated treatment program can significantly attenuate the disease symptoms in autism spectrum disorder, if the disease diagnosis can be made in early phase. However, it is very difficult to diagnose the onset of the disorders by analyzing behavioral patterns during the early infancy, because of the difficulties in differentiating disease symptoms from normal developmental behaviors. Therefore, a biomarker which can be used as an objective marker for diagnosis is required. As an example of a biomarker, Korean Patent No. 10-1096487 discloses a method of diagnosing autism using an amino acid sequence having a specific molecular weight.

SUMMARY OF THE INVENTION

Related Art Document

Patent Document (Patent Document 0001) Korean Patent No. 10-1096487

DISCLOSURE OF THE INVENTION

Problem to be Solved

The present disclosure provides a method for predicting or diagnosing psychiatric disorders based on an objective biomarker.

Means for Solving the Problem

The present disclosure provides a method for predicting or diagnosing psychiatric disorders that that consists of collecting skin tissue from a subject, preparing a sample from skin tissue, analyzing the samples, and comparing the analysis results with those from the healthy skin tissue.

The present disclosure provides a method for predicting or diagnosing psychiatric disorders by non-invasively measuring the skin functions of a subject, such as the trans-epidermal water loss (TEWL), and comparing the measurement data with those from healthy control.

Effects of the Invention

According to the exemplary embodiment of the present disclosure, it can determine whether a subject suffers from a psychiatric disorder using a noninvasive method and it is capable of predicting or diagnosing psychiatric disorders. It is also possible to provide an objective biomarker for predicting or diagnosing psychiatric disorders. In addition, it is possible to treat the psychiatric disorders effectively through early detection and diagnosis because it is capable of determining whether a subject younger than infantry has a psychiatric disorder or not.

BRIEF DESCRIPTION OF THE DRAWING

FIG. 1. shows the molar ratio (C24:1/C16:1) of ceramides among the analysis results of the stratum corneum sample of a k/o mouse and that of a normal mouse.

FIG. 2. shows the molar ratio (C24:1/C16:0) of ceramide among the analysis results of the stratum corneum sample of a k/o mouse and that of a normal mouse.

FIG. 3. shows the molar ratio (C24/C18) of sphingomyelin among the analysis results of the stratum corneum sample of a k/o mouse and that of a normal mouse.

FIG. 4. shows the molar ratio (C24/C20) of sphingomyelin among the analysis results of the stratum corneum sample of a k/o mouse and that of a normal mouse.

FIG. 5 shows the molar ratio (So/Sa) of sphingosine (So) and sphinganin (Sa), the molar ratio (So/S1P) of sphingosine and sphingosine-1-phosphate (S1P), and the molar ratio (Sa/S1P) of sphinganin and sphingosine-1-phosphate among the analysis results of the stratum corneum sample of k/o mouse and that of normal mouse.

FIG. 6. shows the analysis results of ceramide in the brain (A) and the skin (B) of normal and VPA neonatal mice which were one day old (Control: normal neonatal mouse; VPA: The valproic acid-induced mouse model of autism spectrum disorder (ASD)).

FIG. 7. shows the analysis results of sphingomyelin in the brain (A) and the skin (B) of normal and VPA neonatal mice which were one-day old (Control: normal neonatal mouse; VPA: The valproic acid-induced mouse model of autism spectrum disorder (ASD)).

FIG. 8 shows the dynamics of changes in the skin condition of normal and VPA neonatal mice ((A): skin changes on days 1 and day 30 of normal neonates; (B) and (C): skin condition of VPA neonates at day 1; and (D): skin condition of VPA neonates at day 30; scale bar=10 μm).

FIG. 9 shows the difference in trans-epidermal water loss (TEWL) (A) and skin moisturizing degree (B) between a patient with autism and a normal person (No symptoms: a normal person; w/symptoms; a patient with autism).

DETAILED DESCRIPTION OF THE EMBODIMENT

Hereinafter, the present disclosure is described in detail. Throughout the specification, unless defined otherwise, the terms used herein should be interpreted as generally understood by one of ordinary skill in the art. The drawings and embodiments in the present specification are intended for use by those skilled in the art to readily understand and practice the present disclosure. In the drawings and embodiments, contents which may obscure the gist of the disclosure may be omitted and the present disclosure is not limited to the drawings and embodiments.

The present disclosure relates to a method for predicting and diagnosing the psychiatric disorders and can provide an objective biomarker for diagnosing the psychiatric disorders and information using it.

According to the present disclosure, it is possible to predict or diagnose the psychiatric disorders by sampling the skin tissue of a subject, preparing a sample, analyzing the samples, and comparing the analysis results with those from the healthy skin tissue.

A subject is an organism, an individual, or a group supposedly diagnosed as having the psychiatric disorders. A subject is preferably, but not limited to, a person having a high risk of autism because of the familial history. The skin tissue sampling can be done by noninvasive or minimal-invasive methods, so the age, gender, and condition of a subject do not limit the sampling procedure. Tape stripping is an example of a noninvasive method, but it is not limited to it.

A control or a control group indicates an organism, an individual, or a group that does not experience the psychiatric disorders to be predicted or diagnosed. It is possible to collect the skin tissue to prepare a sample and analyze the sample of a subject based on the analysis results of the control sample. A normal human who does not have a psychiatric disorder such as autism is a preferable control, but it is not limited thereto.

According to the present disclosure, it is possible to predict or diagnose the psychiatric disorders only by analyzing biochemical parameters from the horny layer. Thus, sample collection is simple and quick, and does not elicit invasive damage to a subject.

In generally, it is difficult to know whether a subject has a psychiatric disorder such as autism until it can show language expression or behavioral abnormalities externally. It is known that a child with a psychiatric disorder may develop an abnormal behavior from 6 or 12 months of age, but relatively accurate diagnosing methods such as eye tracking method are possible only after 18 or 24 months of age. The brain scanning method using fMRI can be performed in earlier period, but it requires a subject to sleep, which might pose serious adverse event associated with sleeping pills. Another diagnosis method, directly analyzing brain abnormalities by taking cerebrospinal fluid, can cause inevitable pain to a subject and not suitable for children in the neonatal or infant stage.

The present disclosure was invented based on the experimental finding that there is a close relationship between the changes in the lipids of the brain shown in the psychiatric disorders and the changes in the skin lipids. Based on previous findings that abnormalities in lipids composition of brain are associated with the psychiatric disorders, it is possible to diagnose the psychiatric disorders by analyzing the skin lipids.

The analysis results of the skin tissue samples showed that the major biomarkers of diagnosing the psychiatric disorders were sphingolipids, sphingolipid metabolites, and/or sphingolipid metabolic enzymes. In addition to sphingolipids, sphingolipid metabolites, and sphingolipid metabolic enzymes, however, various chemical or biological substances included in the samples can be also used as biomarkers. Comparison of analysis results can be made based on either single component analysis or combination of two or more components. According to the exemplary embodiment one of the present disclosure, it is possible to diagnose the psychiatric disorders such as autism by analyzing the skin lipids of infants less than 28 days old or young children younger than 6 or 12 months. The diagnostic method of the present disclosure can diagnose the psychiatric disorders earlier than the developmental disorder diagnosis by the behavior evaluation, which is only possible for children older than 18 or 24 months.

Among the sphingolipids or sphingolipid metabolites, at least one of ceramide, ceramide-1-phosphate, sphingosine, sphingosine-1-phosphate, sphingomyelin, glucosylceramide, galactosylceramide, phytosphingosine, phytosphingosine-1-phosphate, cerebroside, ganglioside, dihydrosphingosine, sulfatide, globoside, and acylglucosylceramide can be used as a biomarker but it is not limited to them.

The method analyzing the sphingolipids and sphingolipid metabolites in the samples is not particularly limited. For example, they may be analyzed by one or more of the analytical methods of gas chromatography-mass spectrometry (GS-MS), liquid chromatography-mass spectrometry (LSMS), matrix-assisted laser desorption/ionization time-of-flight mass spectrometry (MALDI-TOF MS), and time-of-flight secondary ion mass spectrometry (TOFSIMS).

According to the analysis method, the threshold obtained from the analysis results may be different and different thresholds may be used to determine the psychiatric disorders.

For example, it is possible to predict or diagnose the psychiatric disorders by comparing the spectroscopic pattern of a control and that of a subject using a spectroscopic pattern composed of the secondary ion mass (m/z) and the strength in the secondary ion mass (m/z), which can be obtained by analyzing samples with TOF-SIMS. As another example, it is possible to predict or diagnose the psychiatric disorders by analyzing and measuring the components and contents of samples using GS-MS or LS-MS and comparing the contents of a specific component in a control sample with that in a subject sample. Alternatively, it is possible to utilize the molar ratios between specific components in the sample.

According to the present disclosure, there is no special limitation for utilizing various analytical methods and analysis results obtained from them since it is possible to diagnose the psychiatric disorders by comparing the analysis results of sphingolipid metabolites in the skin samples of a subject or a control group.

In general, the criteria for diagnosing the psychiatric disorders may vary depending on the carbon number and bonding type even among substances classified as the same sphingolipid or sphingolipid metabolites. For example, C14 ceramide, C16 ceramide, C16:1 ceramide, C18 ceramide, C18:1 ceramide, C20 ceramide, C20:1 ceramide, C22 ceramide, C22:1 ceramide, C24 ceramide, C24:1 ceramide, C26 ceramide, C26:1 ceramide, C14 sphingomyelin, C16 sphingomyelin, C16:1 sphingomyelin, C18 sphingomyelin, C18:1 sphingomyelin, C20 sphingomyelin, C20:1 sphingomyelin, C22 sphingomyelin, C22:1 sphingomyelin, C24 sphingomyelin, C24:1 sphingomyelin, C26 sphingomyelin, C26:1 sphingomyelin, and others are classified as the same ceramide or sphingomyelin, but they can be used as different ceramide or sphingomyelin depending on the carbon number or the number of double bonds. For example, it is possible to diagnose the psychiatric disorders when the moral ratio of C16:1 ceramide and C24:1 ceramide in the subject sample was lower than that of a control sample or the moral ratio of C16:0 ceramide and C24:1 ceramide in the subject sample was lower than that of a control sample. As another example, it is possible to diagnose the psychiatric disorders when the moral ratio of C18 sphingomyelin and C24 sphingomyelin in the subject sample was lower than that of a control sample or the moral ratio of C20 sphingomyelin and C24 sphingomyelin in the subject sample was lower than that of a control sample. More specifically, according to an exemplary embodiment of the present disclosure, it is possible to diagnose the psychiatric disorders when the content of C24 ceramide and C24:1 ceramide in the skin tissue sample collected from a subject is lower than that collected from a control group. According to another exemplary embodiment of the present disclosure, it is possible to diagnose the psychiatric disorders when the content of C24 sphingomyelin and C24:1 sphingomyelin in the skin tissue sample collected from a subject is lower than that collected from a control group. In particular, more than one of sphingolipids or sphingolipid metabolites selected from the group consisting of C24 ceramide, C24:1 ceramide, C24 sphingomyelin, and C24:1 contained in the skin tissue sample obtained from a subject is significantly lower than that in the skin tissue of a control group and it can be selected as a major biomarker for diagnosing the psychiatric disorders.

When a sphingolipid or a sphingolipid metabolite is used as a biomarker, the contents of one or more compounds can be measured and the measurements can be compared based on the contents of the control sample. In addition to comparing the content of the sphingolipids or the sphingolipid metabolites, the molar ratio of more than two sphingolipids or sphingolipid metabolites can be compared or the analysis results of sphingolipids or sphingolipid metabolites in a sample can be used in various ways. For example, it is possible to diagnose the psychiatric disorders when the molar ratios of sphinganine to sphingosine and sphingosine-1-phosphate to sphingosine in a subject's sample are higher than those in the control sample. Furthermore, it is possible to diagnose the psychiatric disorders when the molar ratio of sphingosine-1-phosphate to sphinganine in a subject's sample is lower than that in the control sample.

Sphingolipid metabolic enzymes are also major biomarkers that can be used to predict or diagnose the psychiatric disorders.

The degree of activity of sphingolipid metabolic enzymes can be different between the control group and a subject because the substrate of the sphingolipid metabolic enzymes in the samples is either the sphingolipid or the sphingolipid metabolite. It is possible to predict and diagnose the psychiatric disorders by analyzing the degree of activity of sphingolipid metabolic enzymes. It is also possible to diagnose the psychiatric disorders more accurately by using it together with the analysis results of sphingolipid metabolites.

One or more of serinepalmitoyltransferase, ceramide synthase 1-6, elongation of very long chain fatty acid (ELOVL), sphingosine kinase, ceramide kinase, sphingomyelinase, beta-glucocerebrosidase, galactocerebrosidase, and their subtypes can be used as a biomarker(s) of a sphingolipid metabolic enzyme(s) but it is not limited thereto.

It is possible to predict or diagnose the psychiatric disorders by measuring the activity of sphingolipid metabolic enzymes. It is possible to determine the psychiatric disorders by measuring the activity of a specific sphingolipid metabolic enzyme. Moreover, it is possible to diagnose the psychiatric disorders more accurately by comparing the measurements of the activities of two or more sphingolipid metabolic enzymes. In addition, it is possible to predict or diagnose the psychiatric disorders more accurately by utilizing the contents of sphingolipid metabolites and the activities of sphingolipid metabolic enzymes complexly.

As long as the skin samples are collected from the same part of a subject and a control, the sampling location of the skin is not particularly limited. The back of a hand, the back of a foot, the arm, or the leg are the preferred locations but it is not limited thereto. Since it is possible to sample noninvasively, the skin sample can be collected from any skin part that is easily exposed to outside.

It is possible to diagnose the psychiatric disorders by sampling the stratum corneum among skin strata. Therefore, the skin tissue sample can be obtained by a noninvasive method such as tape stripping.

According to the present disclosure, it is possible to provide a method of predicting or diagnosing the psychiatric disorders without sampling the skin tissue.

It is possible to provide a method of predicting or diagnosing the psychiatric disorders by comparing the trans epidermal water loss (TEWL) measurements of a subject's skin and the TEWL measurements of a control's skin without sampling the skin tissue.

The epidermal permeability barrier function, which is a function of keratinocyte lipids in the stratum corneum, is revealed by the sphingolipid components such as ceramide. Therefore, the abnormal changes of sphingolipid components in the skin may cause the changes in the epidermal permeability barrier function of the skin. Consequently, it is possible to evaluate the changes in the epidermal permeability barrier function through the TEWL measurements.

TEWL is a noninvasive measure of the amount of water loss from the skin surface over a unit period of a time. It is one of the indicators that can be measured objectively through various measurement equipment and methods.

As one example of the relationship between TEWL measurement and the psychiatric disorders, it is possible to diagnose the psychiatric disorders when the TEWL of the subject's skin is higher than that of the control's skin. In particular, according to the exemplary example of the present disclosure, the TEWL measurements can be used as an objective biomarker and the TEWL of patients with autism is considerably higher than that of a normal person.

That developmental disorders that can occur during the fetal period, the neonatal period, the infant period, or before early childhood and is hard to determine the disorder are preferable for the psychiatric disorders that can be predicted or diagnosed according to the present disclosure. Psychiatric disorders such as autism, developmental disorders, behavioral disorders, attention deficit hyperactivity disorder (ADHD), attention deficit disorder (ADD), depression, mood disorders, delusional disorders, obsessive-compulsive disorders, memory disorders, cognitive disorders, panic attacks, and attention disorders are representative disorders but they are not limited thereto.

The method for diagnosing the psychiatric disorders of the present disclosure can be used for screening medicines in the development of effective medicines for curing the psychiatric disorders such as autism.

Hereinafter, exemplary embodiments of the present disclosure will be described. These exemplary embodiments are only examples for practicing the present disclosure and the present disclosure should not be construed as limited to these embodiments.

Exemplary Embodiment 1

Prediction or Diagnosis of Psychiatric Disorders through Analyzing Sphingolipid in the GABA Knock-Out Mouse Model

Exemplary Embodiment 1-1. Analysis of Sphingolipids in K/O Mouse

A gamma-amino butyric acid (GABA) receptor k/o mouse's brain (The Jackson Laboratory) was washed with 1×PBS and about 10 mg of the brain was prepared. The 800 µl of chloroform, 400 µl of methanol, and 1M HCl 300 µl were added to 10 mg of brain and C17-ceramide (d17:1/C18:0), C17 sphingosine-1-phosphate, and C17 sphingosine were added as internal standard materials and then lipids were extracted for 30 minutes. Thereafter, 10,000×g centrifugation was performed and the chloroform layer was transferred to a new tube. It was, afterward, concentrated using a vacuum concentrator. A sample was prepared by dissolving it in 1000 µl of methanol and 10 µl of the sample was injected into LC-MS/MS to analyze sphingoid. The LC-MS/MS was used in the multiple reaction mode (MRM).

The results of the analysis quantified the measured sphingolipid per wet brain weight (g) in nmol.

Exemplary Embodiment 1-2. Comparison of the Analysis Results of Sphingolipids Analysis of a Mouse with Autism and the Analysis Results of Sphingolipid Metabolite of a Normal Mouse It compared the sphingolipid analysis results of a k/o mouse in Exemplary Embodiment 1-1 with the sphingolipid analysis results of a normal mouse.

The molar ratio of ceramide (C24:1/C16:1) was less than 1.0 (about 0.9) in a k/o mouse and it was greater than 2.5 (about 2.6) in a normal mouse (FIG. 1). The molar ratio of ceramide (C24:1/C16:0) was less than 1.0 (about 0.9) in a k/o mouse and it was about 2.0 in a normal mouse (FIG. 2). In the case of ceramide, it was found that the content of ceramide decreased rapidly in a k/o mouse and that the molar ratio of a specific ceramide also decreased more than that of a normal mouse.

The molar ratio of sphingomyelin (C24/C18) was less than 1.0 (about 0.8) in a k/o mouse and it was more than 1.0 (about 1.1) in a normal mouse (FIG. 3). The molar ratio of sphingomyelin (C24/C20) was less than 1.5 (about 1.3) in a k/o mouse and it was more than 1.5 (about 1.55) in a normal mouse (FIG. 4). The content of sphingomyelin decreased in a k/o mouse more than in a normal mouse and the molar ratio of specific sphingomyelins also decreased in a k/o mouse more than in a normal mouse.

So/Sa, the molar ratio of sphingosine (So) and sphinganine (Sa) among sphingolipids, was about 3 in a k/o mouse, which was higher than that in a normal mouse (about 2). So/S1P, the molar ratio of So and sphingosine-1-phosphate (S1P), was over 15 (about 18) in a k/o mouse, which was higher than that in a normal mouse (less than 15 (about 14)). Sa/Sa1P, the molar ratio of Sa and Sa1P was about 10 in a normal mouse and about 8 in a k/o mouse so it was higher in a normal mouse (FIG. 5). It was confirmed that it is possible to predict or diagnose autism by measuring two or more moral ratios among sphingosine, sphinganine, sphingosine-1-phosphate, and sphinganine-1-phosphate.

Exemplary Embodiment 2

Prediction or Diagnosis of Psychiatric Disorders Through Analyzing Sphingolipid in the Mouse Model of Autism Spectrum Disorder (ASD) Induced by Valproic Acid Treatment

Exemplary Embodiment 2-1. Generation of Mouse Model of ASD Using Valproic Acid It is known that the exposure of pregnant animals to valproic acid gives birth to fetuses with psychiatric disorders, including autism. The probability of giving birth to fetuses with psychiatric disorders increases several or tens of times more when the mother is exposed to due to valproic acid (Nicolini, C., Fahnestock, M., The valproic acid-induced rodent model of autism, Exp. Neurol. (2017)).

In this exemplary embodiment, neonate with ASD was obtained by exposing a pregnant mouse to valproic acid (VPA) and this VPA-induced ASD model was employed in all subsequent studies described below.

The 10 mg/kg of valproic acid was administered hypodermically to a female BALB/c mouse during pregnancy (about 10 to 12 days of gestation) and it was fed under normal circumstances to induce the birth. The newborn mice were divided into two groups, A and B. The ceramide in the skin and the brain of new born mice in the group A was analyzed at one day after they were born. The ceramide in the skin and the brain of newborn mice in the group B was analyzed at 14 days after they were born. The neonatal mice without exposing valproic acid were used as a normal control group.

Exemplary Embodiment 2-2. Analyzing Lipid in the Brain and the Skin Collected from the Valproic Acid-Induced Mouse Model of Autism Spectrum Disorder (ASD)

The lipid in the brain and the skin of neonates was analyzed using the same method used in the exemplary embodiment 1. The skin ceramide analysis of the neonatal mice was performed by conducting tape-stripping using the D-Square tape (Cu-Derm Corporation, Dallas, USA) to obtain the skin stratum corneum. 800 µl of chloroform, 400 µl of methanol, and 300 µl 1M HCl were added to the collected D-Square tape and C17-ceramide (d17:1/C18:0), C17 sphingosine-1-phosphate, and C17 sphingosine were as internal standard materials. Afterward, lipid components were extracted for 30 minutes. Thereafter, 10,000×g centrifugation was performed and the chloroform layer was transferred to a new tube. It was, afterward, concentrated using a vacuum concentrator. A sample was prepared by dissolving it in 1000 µl of methanol and 10 µl of the sample was injected into LC-MS/MS to analyze sphingoid. The LC-MS/MS was used in the multiple reaction mode (MRM).

In order to use the analysis results of the brain and the skin to the analysis, the results were quantified based on the extracted protein (pmol/extract protein (mg)).

In the autism induced one-day-old baby mice model, the analysis results of ceramide in the brain and the skin showed specific results of an autism model. The ceramide of the brain and the skin showed that C24:1 ceramide, C24 ceramide, C26:1 ceramide and C26 ceramide, which are ceramides with a long N-acyl chain, decreased compared to a control group (normal baby mice not without autism). The ceramide analysis results of the brain revealed that C16 ceramide increased and C18 ceramide did not show much change. The ceramide analysis results of the skin indicated that C16 ceramide, C16:1 ceramide, and C18 ceramide tended to increase. In particular, the decrease of C24:1 ceramide and C24 ceramide in the brain and the skin tended to be significantly reduced compared to the control (normal baby mice) (FIG. 6).

In the autism induced one-day-old baby mice model, the analysis results of sphingomyelin in the brain and the skin showed specific results of an autism model. The sphingomyelin of the brain and the skin showed that C24:1 sphingomyelin, C24 sphingomyelin, C26:1 sphingomyelin, and C26 sphingomyelin, which are sphingomyelin with a long N-acyl chain, decreased compared to a control group (normal baby mice not without autism). The sphingomyelin analysis results of the brain revealed that C16 sphingomyelin and C18 sphingomyelin increased. The sphingomyelin analysis results of the skin indicated that C18 sphingomyelin tended to increase. In particular, the decrease of C24:1 sphingomyelin and C24 sphingomyelin in the brain and the skin tended to be significantly reduced compared to the control (normal baby mice) (FIG. 7).

The dynamics of the skin sphingolipid was evaluated at 1 day and 14 days after birth and the results showed that the changes in the skin sphingolipid were high at 1 day after birth but the changes in it were less at 14 days after birth compared to that at 1 day after birth. The differences in the changes of sphingolipid according to the number of days of birth prove that the accuracy of diagnosis of the psychiatric disorders such as autism increases when the lipid analysis is conducted sooner. Moreover, the results show that the psychiatric disorders such as autism can be diagnosed early even within 1 or 2 weeks from birth.

It has confirmed from these results that an animal with the psychiatric disorders such as autism has very similar lipid composition in the brain and the skin.

These results showed that it is possible to diagnose the psychiatric disorders such as autism early in life by using non-invasive or minimal-invasive methods such as a skin sampling method instead of using an invasive method accompanying with pain such as spinal fluid sampling or brain collection.

Exemplary Embodiment 2-3. Skin and Brain Biopsies of the Valproic Acid-Induced Mouse Model of Autism Spectrum Disorder (ASD)

The skin and brain tissues of neonates with ASD were observed under an electron microscope. The skin and brain tissues of one day and 30 days old neonatal mice were observed.

The observation results showed that an abnormal tissue development pattern was found in both brain and skin tissues of autism-induced baby mice with developmental disorders at one day after birth. However, these abnormal tissues were improved 30 days after birth (FIG. 8).

These results support that the accuracy of diagnosis of the psychiatric disorders such as autism increases when the lipid analysis is conducted sooner. Moreover, the results show that the psychiatric disorders such as autism can be diagnosed early even within 1 or 2 weeks from birth.

Exemplary Embodiment 3

Prediction or Diagnosis of Psychiatric Disorders Through TEWL Measurement

Trans-epidermal water loss (TEWL) and skin hydration were measured at the inside of arms of 25 patients with autism (developmental disorder patients) and normal people. TEWL ($g/h/m^2$) and skin hydration (arbitrary Corneometer® units) were measured by connecting TM300, a probe to measure TEWL, and CM825, a probe to measure skin hydration, to the MPA5 device (Courage & Khazaka, Cologne, Germany). The mean age of the subjects was 19.2 years.

The measurement results showed that the TEWL of patients with autism was significantly higher than that of normal people and the former had a much weaker skin hydration function than the latter (FIG. 9).

These results show that the skin barrier function of patients with autism is deteriorated more than that of normal people and that it is possible to diagnose patients with autism by measuring the skin barrier function such as TEWL and skin hydration along with analyzing skin lipids.

What is claimed is:

1. A method for determining a sphingolipid ratio in a subject that comprises:
   preparing a skin tissue sample obtained from the subject, wherein preparing the skin tissue sample includes extracting lipid components,
   analyzing a sphingolipid or sphingolipid metabolite content of the skin tissue sample by running the sphingolipid or sphingolipid metabolite content of the skin tissue sample in one or more of gas chromatography-mass spectrometry (GS-MS), liquid chromatography-mass spectrometry (LS-MS), matrix assisted laser desorption/ionization time-of-flight mass spectrometry (MALDI-TOF MS), and time-of-flight secondary Ion mass spectrometry (TOF-SIMS),
   providing a control subject who has a healthy control skin,
   comparing the sphingolipid or sphingolipid metabolite content from the subject with those obtained from the healthy control skin,
   and
   obtaining the sphingolipid ratio, the sphingolipid ratio being a molar ratio of a first sphingolipid of the skin tissue sample to a second sphingolipid of the skin tissue sample,
   wherein the skin tissue sample is obtained by a tape stripping method,
   and
   wherein the molar ratio is a molar ratio of C24:1/C16:1 ceramides, C24:1/C16:0 ceramides, C24/C18 sphingomyelins, or C24/C20 sphingomyelins.

2. The method of claim 1, wherein analyzing the sphingolipid or sphingolipid metabolite content of the skin tissue sample includes analyzing a sphingomyelin content of the skin tissue sample.

3. The method of claim 1, wherein the skin tissue sample is a stratum corneum.

* * * * *